United States Patent [19]

Geller

[11] Patent Number: 4,534,757

[45] Date of Patent: Aug. 13, 1985

[54] DEVICE FOR RELEASING ACTIVE INGREDIENT, INSERTABLE IN A SYSTEM OF PARENTERAL ADMINISTERING THE INGREDIENT

[75] Inventor: Leo Geller, Riehen, Switzerland

[73] Assignee: ALZA Corporation, Palo Alto, Calif.

[21] Appl. No.: 500,744

[22] Filed: Jun. 3, 1983

[30] Foreign Application Priority Data

Jun. 14, 1982 [CH] Switzerland .......................... 3668/82
Jul. 2, 1982 [CH] Switzerland .......................... 4051/82

[51] Int. Cl.³ .............................................. A61M 5/00
[52] U.S. Cl. ...................................... 604/85; 604/126; 604/246
[58] Field of Search ....................... 604/82, 83, 84, 85, 604/86, 126, 246, 251, 252, 253, 254, 257, 406, 416

[56] References Cited

U.S. PATENT DOCUMENTS 4,439,183 3/1984 Theeuwes ........................ 604/251 X
4,474,574 10/1984 Wolfe et al. ........................... 604/85

Primary Examiner—W. J. Shine
Attorney, Agent, or Firm—Sabatine, Paul L.; Mandell, Edward L.; Steven F. Stone

[57] ABSTRACT

A device for releasing active ingredient into a liquid flow passing through a system for parenteral application of the ingredient comprises a receptacle composed of two half shells. The receptacle is subdivided by a ribbed aluminium foil into two chambers and has an inlet at its upper end and an outlet at its lower end. The two chambers have vent means at their upper ends. One of the chambers contains two overflows a first one of which empties into the outlet while the second one empties into the other chamber. In the latter chamber there is present a further overflow which also empties into the outlet, as well as a plate-shaped carrier charged with the active ingredient to be released. The liquid flows from the inlet via the first chamber and the second overflow therein into the other chamber and from there upwardly past a carrier charged with active ingredient, and onward via a third overflow in the other chamber into the outlet. In a second flow path, part of the liquid flows directly from the inlet through the first chamber and via the first overflow therein into the outlet.

This device permits a very uniform release of active agent and is of simple construction and correspondingly it can be manufactured in an inexpensive manner.

10 Claims, 6 Drawing Figures

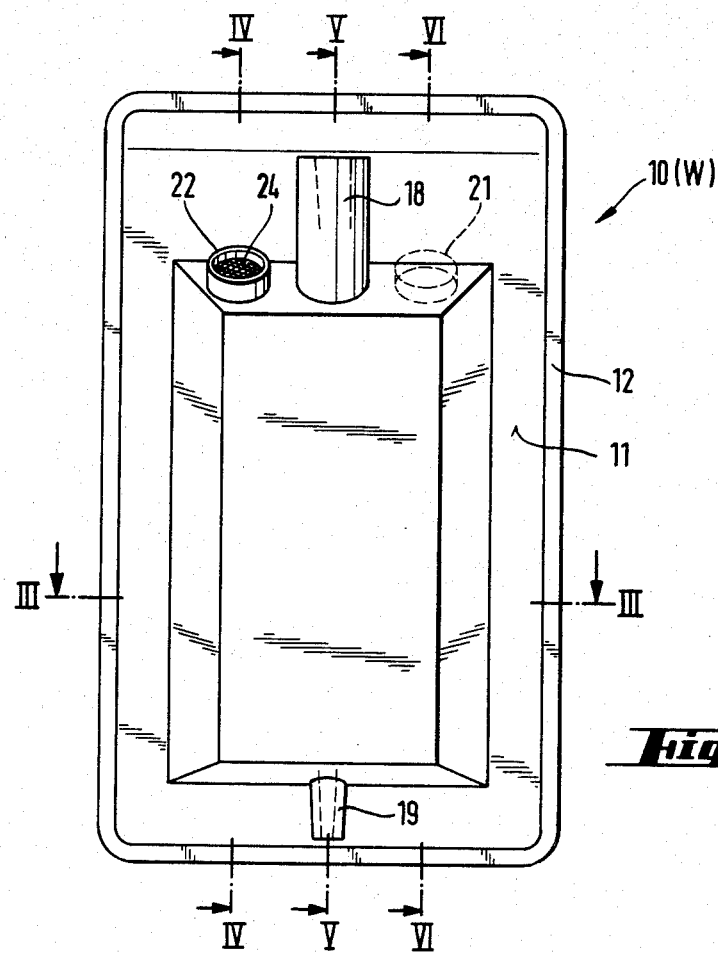
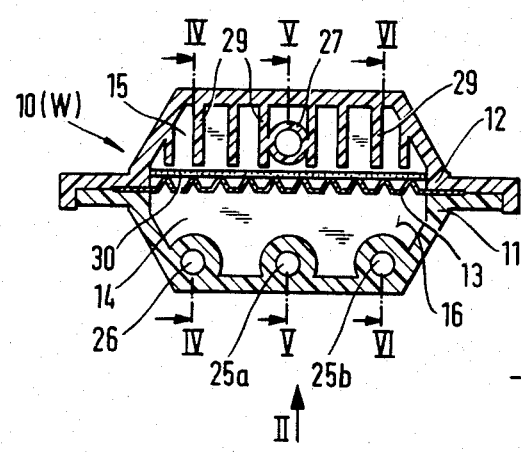

DEVICE FOR RELEASING ACTIVE INGREDIENT, INSERTABLE IN A SYSTEM OF PARENTERAL ADMINISTERING THE INGREDIENT

BACKGROUND OF THE INVENTION

This invention relates to a device for releasing active ingredient, which device is insertable in the liquid flow line of a system for the parenteral application of the ingredient, and comprise a receptacle having an inlet and an outlet for a liquid flow passing therethrough, and ingredient-releasing means, lodged in the receptacle, for releasing active ingredient into the said liquid flow.

The intravenous adminstration of liquids such as blood, blood substitute and other infusion solutions is an important aspect of the medical treatment of patients. In many cases, simultaneously or together with the infusion solution, another medicament is administered intravenously, in a number of different systems existing for this purpose. For instance, in a system of this type described in U.S. patent application Ser. Nos. 289,082, now abandoned 310,047, 312,491, and 325, 206, now U.S. Pat. No. 4,432,756 issued Feb. 21, 1984, published together in DE-OS 32 28 595, there is inserted, in the infusion flow line or a bypass thereof, a receptacle containing the active ingredient to be administered in a specially adapted formulation (osmosis system) guaranteeing a release of active ingredient into the infusion solution during a prolonged period of time. A drawback of this system consists primarily in that the active ingredient must always be present in a special formulation and that, in particular, the insertion of the receptacle in the infusion flow line is relatively complicated, especially when it is to be made in a bypass line. A further drawback of the known system resides in the fact that it is relatively difficult to remove from the receptacle any air that may be present therein.

OBJECTS AND SUMMARY OF THE INVENTION

Objects of the present invention are to provide an improved active ingredient-releasing device of the initially described kind, which, on the one hand, guarantees a satisfactory, even and controlled release of the active ingredient, without requiring the ingredient to be in a specific formulation, and, on the other hand, is of simple construction, operation and service, and lastly, that no difficulties occur in emptying the device of air.

The active ingredient-releasing device of the initially described type, is improved, in accordance with the invention, by comprising in the receptacle two liquid flow paths leasing from the inlet to the outlet thereof, one of which paths comprises a section through which the liquid passes in a direction substantially opposite to a general direction in which the receptacle is passed by the liquid, and an ingredient-releasing unit being present in the said path section of opposite liquid flow.

In a preferred embodiment of the device according to the invention, the receptacle comprises two communicating chambers each of which is provided with an overflow empty-ing into the outlet, and the inlet leads into the upper part of a first one of the chambers while the ingredientreleasing unit is located in the second one of said chambers.

According to another preferred feature of the device according to the invention, the two chambers communicate with one another via a further overflow which empties into the lower part of the said other chamber.

Preferably, the receptacle consists of two shells of synthetic plastics each of which is preferably made of one piece.

The receptacle can be subdivided by a transverse separating wall such as a foil, especially a foil made of ribbed aluminium, which has a peripheral zone clamped in between the two plastics half shells.

In its upper part, on the side of the entry, the device can be provided with an air vent equipped with a filter being pervious essentially for gases only. The ingredient-releasing unit can be devised as a plate-shaped carrier on or in which the active ingredient is lodged. Finally, the receptacle can be provided with holding means such as vanes or ribs for supporting and/or holding in position the ingredient-releasing unit in the interior of the chamber destined for containing the same.

BRIEF DESCRIPTION OF THE DRAWINGS

A preferred embodiment of the device according to the invention will be explained more in detail, and further objects of the invention will become apparent from the following description of the accompanying drawings in which FIG. 2 is a top view of the embodiment of an ingredient-releasing device shown in FIG. 1, and FIGS. 3 to 6 are sectional views of the same embodiment, taken in planes indicated by III—III, IV—IV, V—V and VI—VI, respectively, shown in FIG. 2.

DETAILED DESCRIPTION OF THE EMBODIMENT SHOWN IN THE DRAWING

Figure 1:
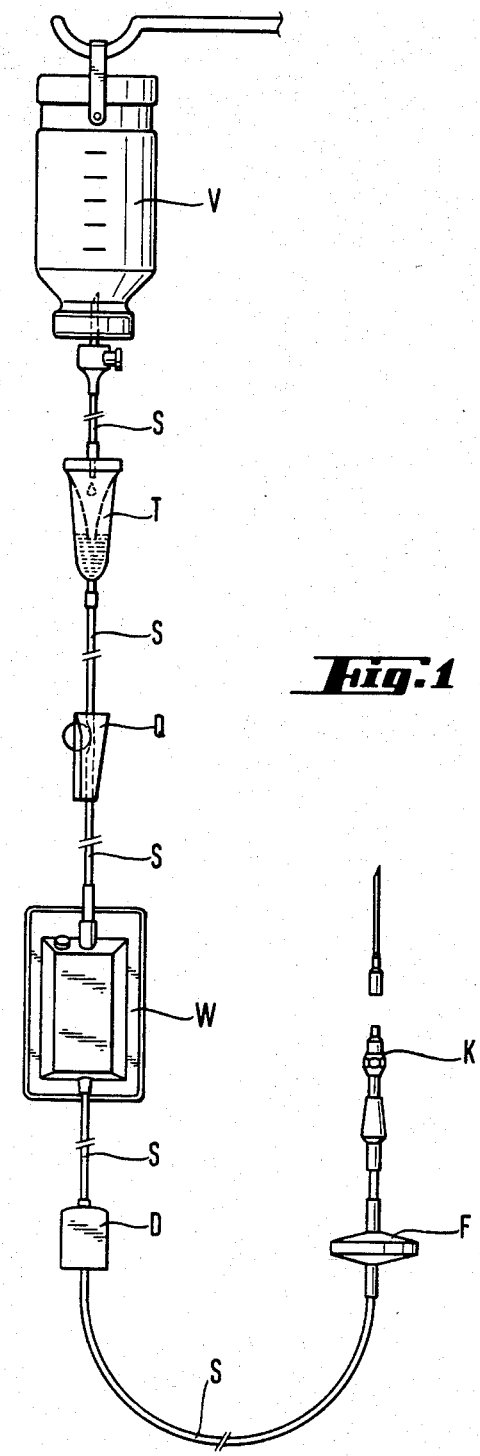
FIG. 1 is a schematic view of a paraenteral administering system equipped with an active ingredient-releasing device according to the invention.

The parenteral administering system shown by way of example in FIG.1 comprises in a typical manner a storage receptacle V for liquid to be administered, for instance, a physiological sodium chloride solution or the like, a dripping device T, a squeezer Q, an ingredient-releasing unit W, a flow-limit control D, a sterile filter F, a hollow needle K and hose means S connecting all these parts with one another in series. The specific design of the individual elements of the system, with the exception of the ingredient-releasing unit W, is conventional and a detailed description thereof can therefore be dispensed with as superfluous for the understanding of the instant invention.

As described thus far, the system corresponds essentially to that known from the description of DE-OS 32 28 595. What is different is the concept of the ingredient-releasing unit W, details of whose construction are illustrated in FIGS. 2-6.

The unit W comprises a receptacle 10 composed of two plastics half-shells 11 and 12. The receptacle 10 is subdivided into two chambers 14 and 15 by means of a ribbed aluminum foil 13 at least part of the circumferential edge of which is clamped in between the two half shells 11 and 12. A bottom wall 16 separates a collecting space 17 extending below the two chambers 14 and 15 from these two chambers. A separating wall made of synthetic plastics resin or another material can, of course, be used instead of the aluminum foil 13.

Figure 4:
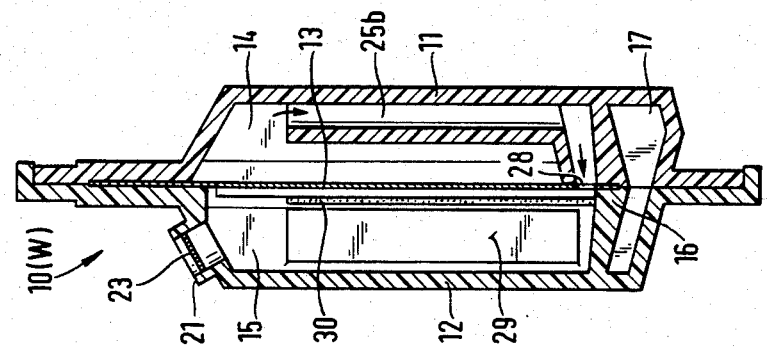
Figure 5:
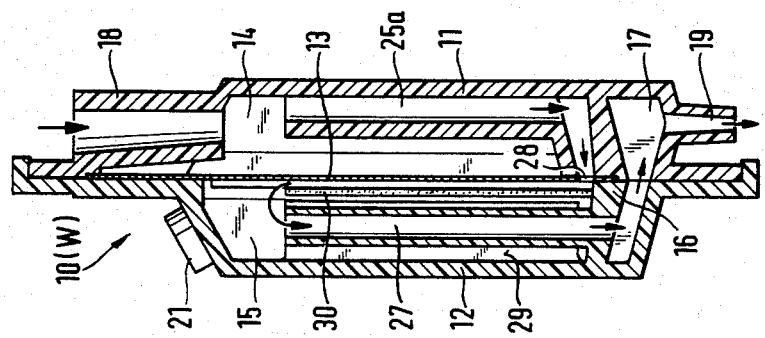
Figure 6:
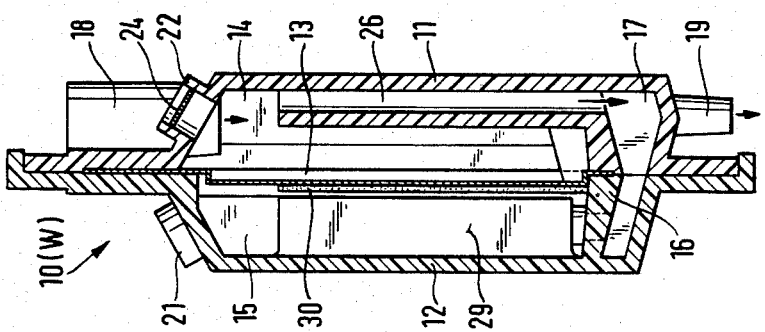

The receptacle half-shell 11, shown as the right hand one in FIGS. 3 to 5 of the drawing, is provided at its upper end with a socket-shaped inlet 18 and its lower end with an exit 19 of similar shape. The inlet 18 and the outlet 19 serve for connection with or insertion in the liquid flow line S and are preferably so devised (not shown) that they can be connected securely with the respective sections of the line S in a simple manner requiring only few stages of assembly by hand (for instance a bayonet catch or the like).

Each of the receptacle half shells 11 and 12 further have a vent 21,22 in the vicinity at their highest point, taken in a vertical position of use, which vent is provided with a preferably hydrophobic filter 23,24, so that air or another gas, but no liquid to be administered can escape through these openings or filters.

Apart from the aluminum separating wall 13 and the bottom wall 16, the receptacle 10 is further more equipped with, as additional fittings, four tubular overflows 25a, 25b, 26 and 27, of which three are located in the righthand chamber 14 and one in the left-hand chamber 15, having reference to the drawing. One of the overflows in the right-hand chamber 14, namely the forwardly located overflow 26, as well as the overflow 27 in the left-hand chamber 15 both empty at their lower end into the collecting space 17 and by way of the latter into the outlet 19. The overflows 25a and 25b empty via openings 28 in the aluminium foil 13, into the bottom zone of the left-hand chamber 15.

Finally, a number of reinforcing ribs 29 are molded integrally with the wall of the left-hand receptacle half shell 12, which ribs, in combination with the ribbed aluminium foil 13 hold fast in position an ingredient-releasing unit 30 which is plate-shaped in this embodiment. This plate-shaped unit 30 consists of a cellulose carrier on or in which the active ingredient to be administered is present in soluble form. Instead of the cellulose carrier, a plate of synthetic plastic resin material can be provided which plate has a recess in which the active ingredient can be lodged.

The device functions as follows:

The liquid to be administered to the patient, for instance a random kind of infusion solution, flows through the inlet 18 into the receptacle 10 and passes through the latter along two different paths in order to leave it again via the outlet 19. The first flow path is a relatively direct one, namely from the inlet 18 into the righthand chamber 14 and onward via the overflow 26 and the collecting space 17 to the outlet 19. The second flow path is more complicated. In this path, the liquid passes through the right-hand chamber 14 and via the overflows 25a and 25b into the left-hand chamber 15 and from there via the overflow 27 and the collecting space 17 into the outlet 19. As can be readily seen from the drawing, the section 28-27 of the flow path from prior to entry into the lefthand chamber 15 till the entry opening of the overflow 27 is traversed in upward direction by the liquid, i.e. in a direction which is directly opposite to the general direction of flow, namely downardly, of the liquid. It is in this section through which the liquid flows in opposite, inverted direction that the active ingredient-releasing unit 30, i.e. cellulose-carrier charged with the active ingredient, is located. The liquid passing this carrier now dissolves the active ingredient out of the carrier in a controlled manner, a particularly uniform and constant release of active ingredient into the liquid being thus achieved owing to the special arrangement of the carrier.

Any air trapped in the chambers 14 and 15 can then escape through the vents 21 and 22 to the outside.

The through-flow rate and speed of active ingredient release can be adjusted to the prevailing requirements over a broad range by an appropriate dimensioning of the overflows.

By means of the flow limiting control unit D which is arranged downstream of the ingredient-releasing unit W, and which preferably is a capillary flow limit control, it is possible to adjust the flow rate of the infusion solution according to the required rate and in a reproduceable manner. In the foregoing, there has been described merely one, particularly practicable embodiment of the active ingredient-releasing device according to the invention.

It will be understood that numerous variations of the device are possible, which variations are, however, all comprised within the scope of the appended claims. The essential feature resides in the provision of a flow path section through which the liquid flows in a direction opposite to its general direction of flow, and in that the release of active ingredient into the liquid occurs in this section of opposite liquid flow; for, thanks to the reverse liquid flow, there is achieved a certain damming-up effect and thereby a uniform flow rate, which ultimately results in a uniform and constant release of active ingredient. A further essential feature of the device according to the invention resides in the provision of the vents which enable air trapped in the receptacle to escape.

The active ingredient-releasing device according to the invention affords as stated hereinbefore, a very uniform release of active ingredient while being at the same time, of simple construction so that it is very well suited for one-time use and as a throw-away unit, whereas the carrier containing the active ingredient need not be inserted at use only, but can be contained in the ready-made device as of its manufacture.

I claim

1. A device for releasing active ingredient, which device is insertable in the liquid flow line of a system for the parenteral application of the ingredient, and comprises a receptacle having an inlet and outlet for a liquid flow passing therethrough, and ingredient-releasing means, lodged in the receptacle, for releasing active ingredient into the said liquid flow, said receptacle further comprising in its interior two liquid flow paths leading from the inlet to the outlet thereof, one of which paths comprises a section through which the liquid passes in a direction substantially opposite to a general direction in which the receptacle is passed by the liquid, and an ingredient-releasing unit being present in the said path section of opposite liquid flow.

2. The device of claim 1, wherein said receptacle comprises two communicating chambers and, in each of said chambers, an overflow emptying into said outlet, said inlet leading into the upper part of a first one of said chambers while said ingredient-releasing unit is located in the second one of said chambers.

3. The device of claim 2, wherein said receptacle further comprises a further overflow by way of which said two chambers communicate with one another and which further overflow empties into the lower part of said second chamber.

4. The device of claim 2, wherein said receptacle comprises two half shells.

5. The device of claim 4, wherein each of said half shells is an integral piece of artificial plastic resin material.

6. The device of claim 4, wherein said receptacle comprises a separating wall having an edge clamped in between said two half shells and subdividing said receptacle into said two chambers.

7. The device of claim 1, wherein said receptacle comprises in the upper end zone thereof, containing said inlet, vent means and a filter associated with said vent means and being pervious essentially for gases only.

8. The device of claim 1, wherein said ingredient-releasing unit is a plate-shaped carrier being charged with the active ingredient.

9. The device of claim 8, wherein said receptacle has an outer wall and holding means protruding inwardly from said outer wall and being adapted for holding said plateshaped carrier in position in the interior of said receptacle.

10. The device of claim 9, wherein said holding means comprise vanes or ribs.

* * * * *